(12) United States Patent
Ahlberg et al.

(10) Patent No.: US 7,494,501 B2
(45) Date of Patent: Feb. 24, 2009

(54) OVERMOLDED GRASPER JAW

(75) Inventors: Russell E. Ahlberg, Rancho Santa Margarita, CA (US); Scott V. Taylor, Mission Viejo, CA (US); David Okihisa, Irvine, CA (US); Gregory I. Boychuck, Laguna Niguel, CA (US); Emil Karapetian, Trabuco Canyon, CA (US); John Stout, Irvine, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 386 days.

(21) Appl. No.: 10/986,993

(22) Filed: Nov. 12, 2004

(65) Prior Publication Data

US 2005/0101991 A1    May 12, 2005

Related U.S. Application Data

(60) Provisional application No. 60/519,849, filed on Nov. 12, 2003.

(51) Int. Cl.
*A61B 17/28* (2006.01)
(52) U.S. Cl. ..................................... 606/207
(58) Field of Classification Search ............... 606/205, 606/207, 208, 210, 170, 157; 600/564; 24/513, 24/515; 294/106
See application file for complete search history.

(56) References Cited

U.S. PATENT DOCUMENTS 487,068 A    11/1892    Drinkwater (Continued)

FOREIGN PATENT DOCUMENTS

EP    0 584 723 A    3/1994

OTHER PUBLICATIONS

WO 91/02493 published Mar. 7, 1991 entitled "A Device For Grasping Or Cutting An Object".

*Primary Examiner*—Todd E Manahan
*Assistant Examiner*—Ryan Severson
(74) *Attorney, Agent, or Firm*—John F. Heal; David G. Majdali; Patrick Y. Ikehara

(57) ABSTRACT

The invention is directed to a surgical instrument comprising an elongate tube extending along an axis including a camming rod and an actuation mechanism operably connected to the camming rod, the camming rod having a camming pin and a camming projection; a first jaw spine having a first cam slot, a first interior camming surface, and a first exterior camming surface; and a second jaw spine having a second cam slot, a second interior camming surface, and a second exterior camming surface, the second jaw spine pivotally connected to the first jaw spine at a common pivot pin operably connected to the elongate tube to open and close the jaw spines in response to movement of the actuation mechanism. The camming pin rides along the first and second interior camming surfaces and operates to close the jaw spines when the camming rod is moved proximally. When the camming rod moves distally, the camming projection rides on the first and second exterior camming surfaces formed on the proximal sides of the respective first and second jaw spines and operates to open the jaw spines. A feature of the invention is one camming surface on each jaw spine can facilitate closing the jaw spines while the other camming surface on each jaw spine can facilitate opening the jaw spines. These two camming surfaces on each jaw spine can be widely separated. The jaw spines can be formed of a metallic material and are overmolded with an atraumatic plastic material. By overmolding the plastic onto the metal spine, an atraumatic outer surface can be formed of the plastic material along with a high degree of detail.

14 Claims, 9 Drawing Sheets

U.S. PATENT DOCUMENTS

| | | | |
|---|---|---|---|
| 1,746,221 A * | 2/1930 | Matteson | 226/173 |
| 1,754,806 A | 4/1930 | Stevenson | |
| 1,956,588 A | 5/1934 | Parker et al. | |
| 2,002,594 A | 5/1935 | Wappler et al. | |
| 2,034,785 A | 3/1936 | Wappler | |
| 2,618,268 A | 11/1952 | English | |
| 2,790,437 A | 4/1957 | Moore | |
| 3,101,715 A | 8/1963 | Glassman | |
| 3,404,677 A | 10/1968 | Springer | |
| 3,446,211 A | 5/1969 | Markham | |
| 3,562,908 A | 2/1971 | Rogers | |
| 3,585,985 A | 6/1971 | Gould | |
| 3,595,188 A * | 7/1971 | Schmedding et al. | 112/221 |
| 3,735,763 A | 5/1973 | Shannon et al. | |
| 3,807,406 A | 4/1974 | Rafferty et al. | |
| 3,840,003 A | 10/1974 | Komiya | |
| 3,871,379 A | 3/1975 | Clarke | |
| 3,895,636 A | 7/1975 | Schmidt | |
| 3,964,468 A | 6/1976 | Schulz | |
| 3,995,619 A | 12/1976 | Glatzer | |
| 4,005,714 A | 2/1977 | Hiltebrandt | |
| 4,038,987 A | 8/1977 | Komiya | |
| 4,043,343 A | 8/1977 | Williams | |
| 4,054,143 A | 10/1977 | Bauer | |
| 4,064,881 A | 12/1977 | Meredith | |
| 4,122,856 A | 10/1978 | Mosior et al. | |
| 4,128,099 A | 12/1978 | Bauer | |
| 4,169,476 A | 10/1979 | Hiltebrandt | |
| 4,201,213 A | 5/1980 | Townsend | |
| 4,243,047 A | 1/1981 | Olsen | |
| 4,282,884 A | 8/1981 | Boebel | |
| 4,345,589 A | 8/1982 | Hiltebrandt | |
| 4,369,788 A | 1/1983 | Goald | |
| 4,420,884 A | 12/1983 | Hembling | |
| 4,433,687 A | 2/1984 | Burke et al. | |
| 4,474,174 A | 10/1984 | Petruzzi | |
| 4,512,343 A | 4/1985 | Falk et al. | |
| 4,522,206 A | 6/1985 | Whipple et al. | |
| 4,569,131 A | 2/1986 | Falk et al. | |
| 4,572,185 A | 2/1986 | Rich | |
| 4,574,802 A | 3/1986 | Straub | |
| 4,590,936 A | 5/1986 | Straub et al. | |
| 4,643,190 A | 2/1987 | Heimberger | |
| 4,646,751 A | 3/1987 | Maslanka | |
| 4,662,371 A | 5/1987 | Whipple et al. | |
| 4,669,470 A | 6/1987 | Brandfield | |
| 4,669,471 A | 6/1987 | Hayashi | |
| 4,674,501 A | 6/1987 | Greenberg | |
| 4,712,545 A | 12/1987 | Honkanen | |
| 4,721,116 A | 1/1988 | Schintgen et al. | |
| 4,759,364 A | 7/1988 | Boebel | |
| 4,763,668 A | 8/1988 | Macek et al. | |
| 4,763,669 A | 8/1988 | Jaeger | |
| 4,785,825 A | 11/1988 | Romaniuk et al. | |
| 4,819,633 A | 4/1989 | Bauer et al. | |
| 4,872,456 A | 10/1989 | Hasson | |
| 4,877,026 A | 10/1989 | de Laforcade | |
| 4,881,550 A | 11/1989 | Kothe | |
| 4,887,612 A | 12/1989 | Esser et al. | |
| 4,896,678 A | 1/1990 | Ogawa | |
| 4,898,157 A | 2/1990 | Messroghli et al. | |
| 4,919,152 A | 4/1990 | Ger | |
| 4,938,214 A | 7/1990 | Specht et al. | |
| 4,944,093 A | 7/1990 | Falk | |
| 4,950,273 A | 8/1990 | Briggs | |
| 4,976,723 A | 12/1990 | Schad | |
| 4,986,825 A | 1/1991 | Bays et al. | |
| 4,994,024 A | 2/1991 | Falk | |
| 5,009,661 A | 4/1991 | Michelson | |
| 5,052,402 A | 10/1991 | Bencini et al. | |
| 5,133,727 A | 7/1992 | Bales et al. | |
| 5,141,519 A | 8/1992 | Smith et al. | |
| 5,152,780 A | 10/1992 | Honkanen et al. | |
| 5,171,256 A | 12/1992 | Smith et al. | |
| 5,171,258 A | 12/1992 | Bales et al. | |
| 5,312,434 A | 5/1994 | Crainich | |
| 5,320,636 A | 6/1994 | Slater | |
| 5,478,347 A | 12/1995 | Aranyi | |
| 5,478,351 A | 12/1995 | Meade et al. | |
| 5,556,416 A | 9/1996 | Clark et al. | |
| 5,591,182 A * | 1/1997 | Johnson | 606/151 |
| 5,632,746 A * | 5/1997 | Middleman et al. | 606/78 |
| 5,662,676 A | 9/1997 | Koninckx | |
| 6,001,096 A | 12/1999 | Bissinger et al. | |
| 6,168,605 B1 | 1/2001 | Measamer et al. | |

OTHER PUBLICATIONS

WO 89/10093 published Nov. 2, 1989 entitled "Endoscopic Biopsy Forceps Device".
Co-Pending U.S. Appl. No. 11/954,457, filed Dec. 12, 2007; Title: Surgical Clip.
Co-Pending U.S. Appl. No. 10/935,967, filed Sep. 8, 2004; Title: Surgical Clip.
Co-Pending U.S. Appl. No. 10/612,631, filed Jul. 2, 2003; Title: Interlocking Suture Clinch.
Co-Pending U.S. Appl. No. 10/533,398, filed Apr. 30, 2005; Title: Surgical Staple-Clip and Applier.
Co-Pending U.S. Appl. No. 11/280,098, filed Nov. 15, 2005; Title: Partial Occlusion Surgical Guide Clip.
Co-Pending U.S. Appl. No. 10/702,871, filed Nov. 5, 2003; Title: Suture Securing Device and Method.
Co-Pending U.S. Appl. No. 10/543,800, filed Jul. 29, 2005; Title: Spring Clip and Method for Assembling Same.
Co-Pending U.S. Appl. No. 10/817,259, filed Apr. 2, 2004; Title: Suture Clip With Stop Ribs and Method for Making Same.

\* cited by examiner

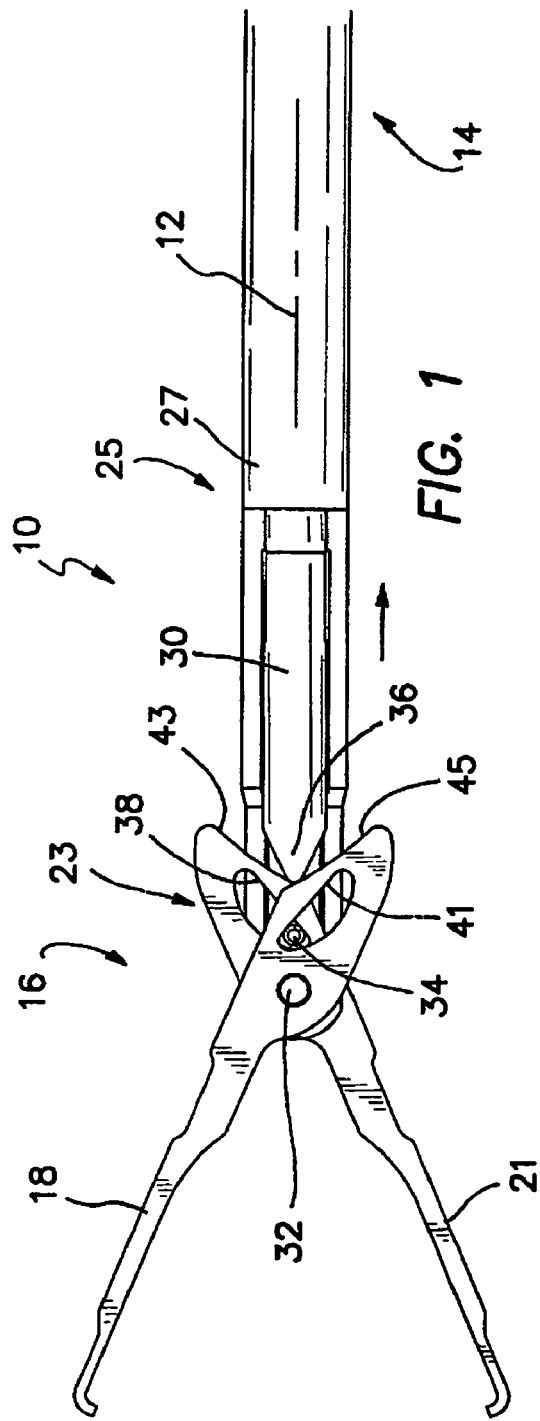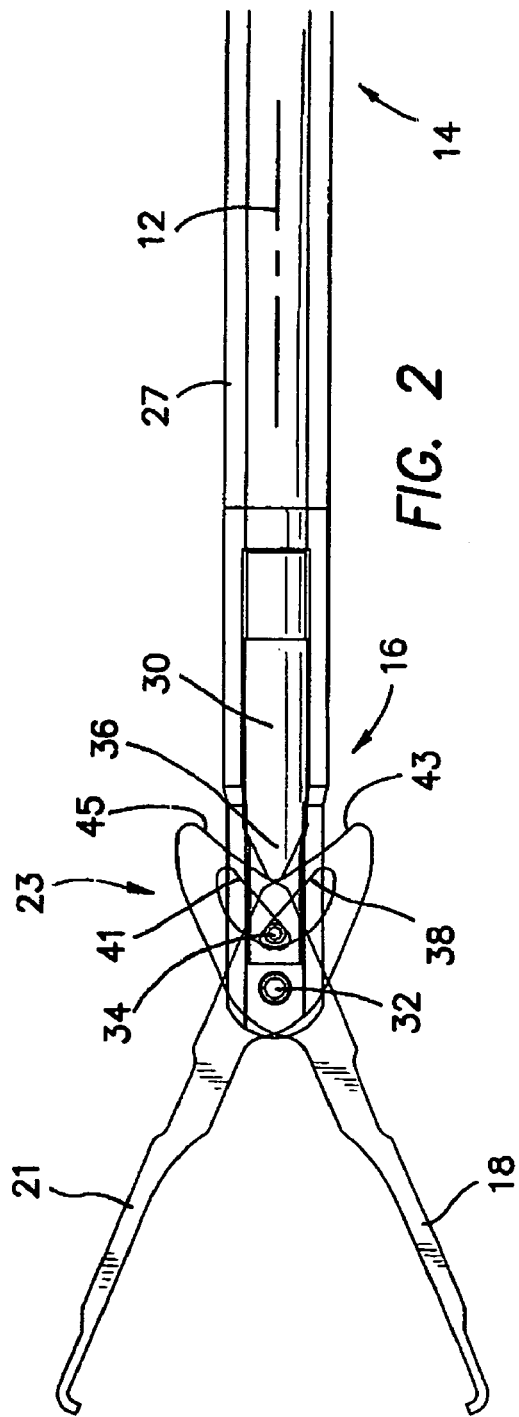

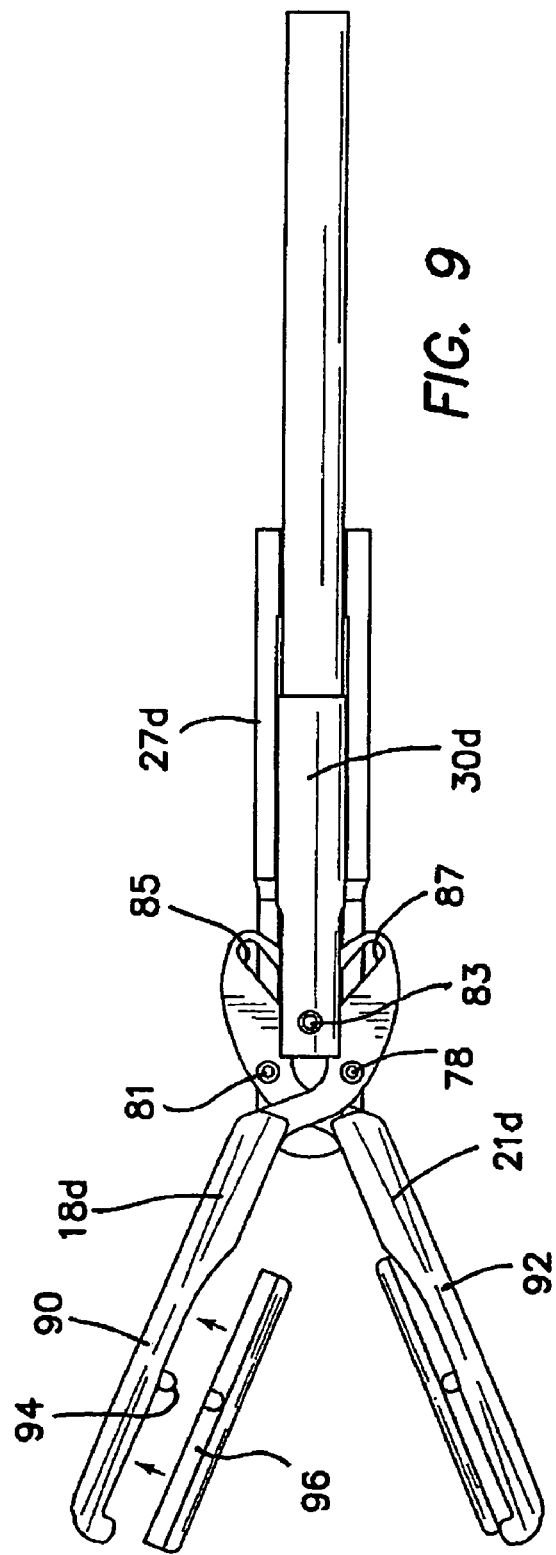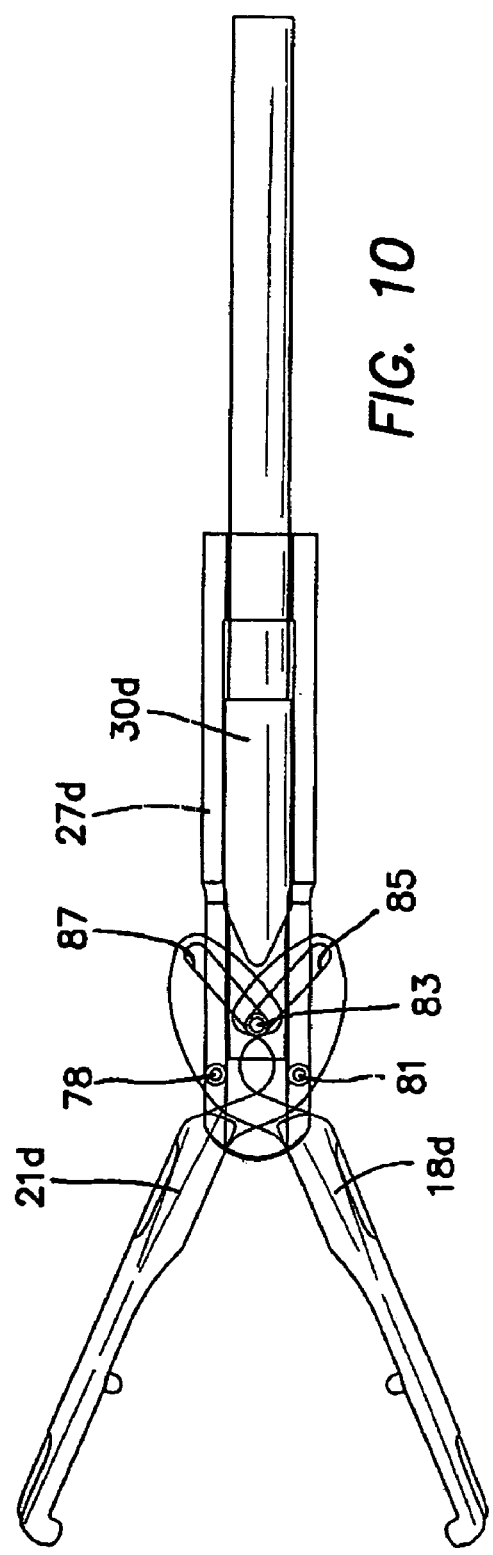

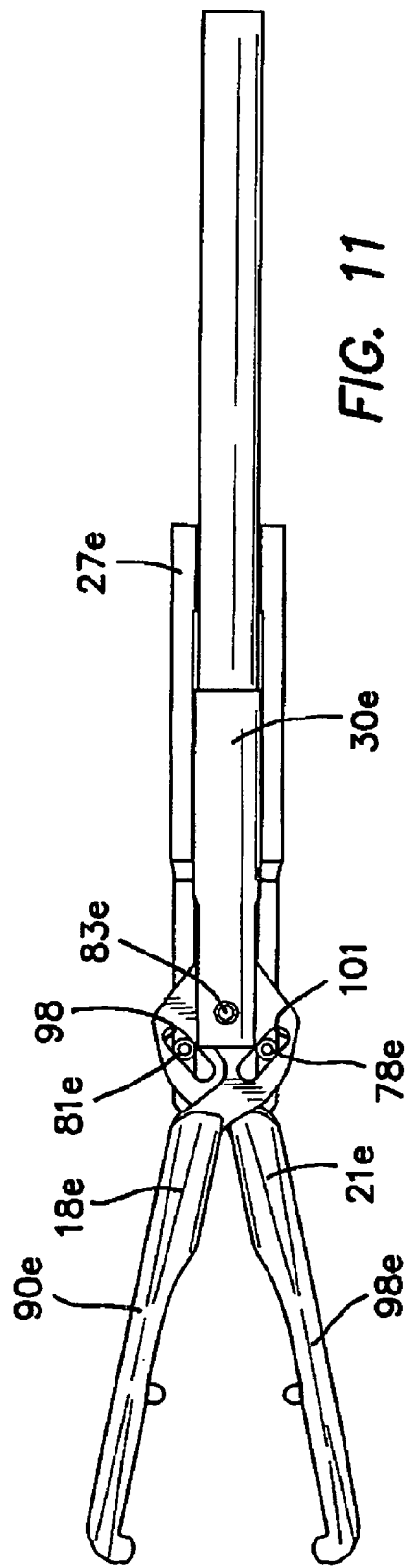
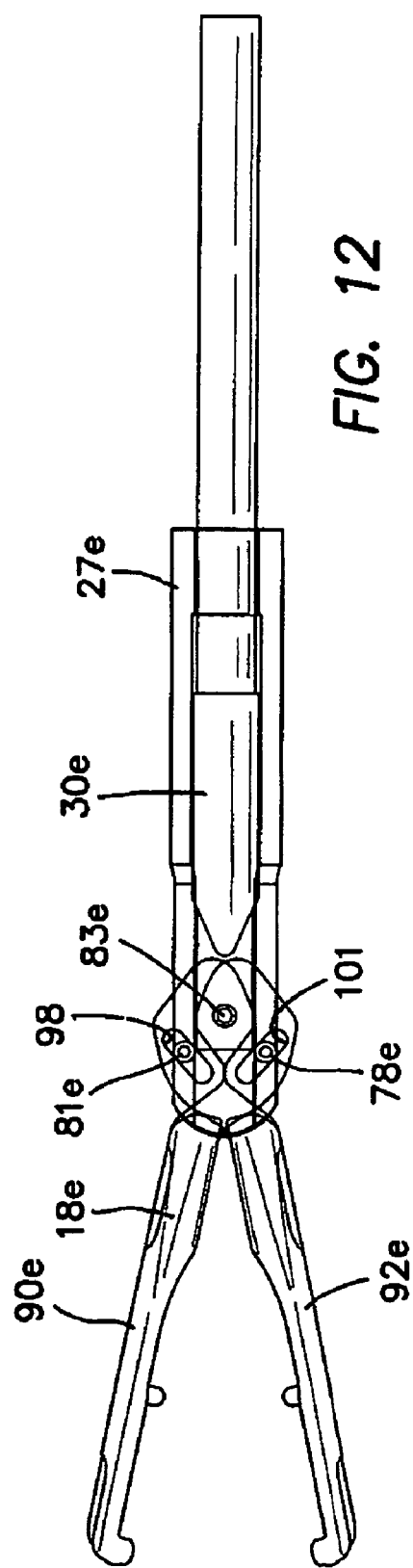

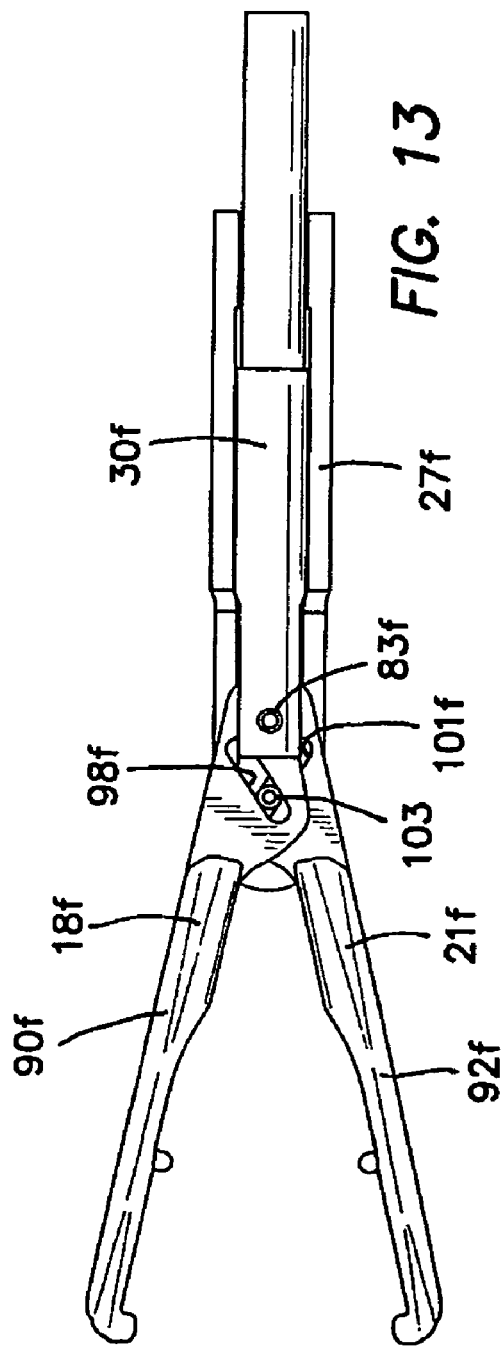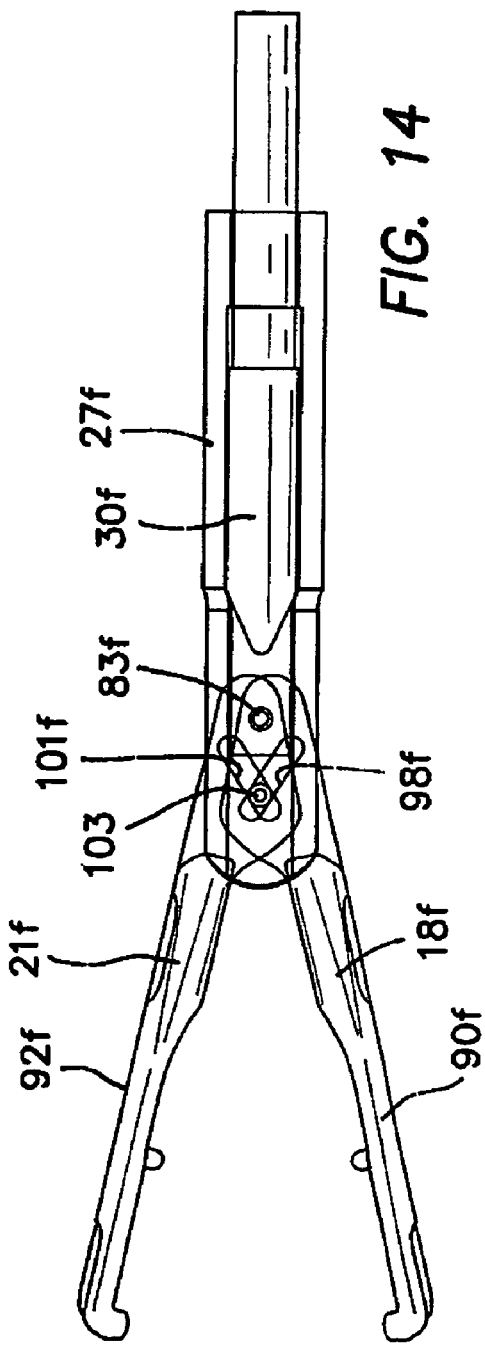

OVERMOLDED GRASPER JAW

This is a non-provisional application claiming the priority of provisional application Ser. No. 60/519,849, filed on Nov. 12, 2003, entitled "Overmolded Grasper Jaw and Double Camming Actuation Mechanism," which is fully incorporated herein by reference.

BACKGROUND OF THE INVENTION

1. Field of the Invention

This invention generally relates to surgical graspers having opposing jaws and, in particular, to composite grasper jaws and mechanisms for actuating the jaws.

2. Discussion of Related Art

In the past, grasper jaws have been formed of metal in order to provide strength and reliability. Various processes of forming the metal have included stamping, EDM (Electrical Discharge Machining), photochemical etching, water jet cutting, laser cutting, and machining. All of these processes are relatively expensive and time consuming since the jaws must end up with outer surfaces and edges which are atraumatic to body tissue. In addition, the actuation mechanisms of the past have typically operated with a single pin moveable axially within two slots, each associated with one of the jaws. The two slots have provided four camming surfaces to open and close each of the two jaws.

SUMMARY OF THE INVENTION

The present invention is directed to a surgical instrument such as a surgical grasper comprising an elongate tube extending along an axis including a camming rod and an actuation mechanism operably connected to the camming rod, the camming rod having a camming pin and a camming projection; a first jaw spine having a first cam slot, a first interior camming surface, and a first exterior camming surface; and a second jaw spine having a second cam slot, a second interior camming surface, and a second exterior camming surface, the second jaw spine pivotally connected to the first jaw spine at a common pivot pin operably connected to the elongate tube to open and close the jaw spines in response to movement of the actuation mechanism.

A feature of the invention is the camming pin rides along the first and second interior camming surfaces and operates to close the jaw spines when the camming rod is moved proximally. With this aspect, the first exterior camming surface is formed on the proximal side of the first jaw spine, the second exterior camming surface is formed on the proximal side of the second jaw spine, and when the camming rod moves distally, the camming projection rides on the first and second exterior camming surfaces and operates to open the respective first and second jaw spines. In other words, one camming surface on each jaw spine can facilitate closing the jaw spines while the other camming surface on each jaw spine can facilitate opening the jaw spines. These two camming surfaces on each jaw spine can be widely separated to provide different mechanical advantages for the opening and closing operations. With this aspect, the closing camming surfaces can be positioned further from the common pivot point to provide an increase mechanical advantage for opening the jaw spines. This is particularly beneficial during a surgical procedure involving the blunt dissection of tissue. The different mechanical advantages also can be tailored to accommodate the different loads encountered when closing and opening the jaw spines.

The jaw spines can be formed of a metallic material and are overmolded with an atraumatic plastic material. The combination of the metal spine and plastic overmold provide a very rigid composite jaw while accommodating relatively inexpensive manufacturing technologies. For example, the jaw spines do not need to be manufactured with a process demanding an atraumatic outer surface. By overmolding the plastic onto the metal spine, an atraumatic outer surface can be formed of the plastic material along with a high degree of detail. Additionally, the overmolded jaws can be provided with features that facilitate application of atraumatic pads.

In another aspect, the invention is directed to a surgical instrument comprising an elongate tube extending along an axis including an actuation rod; a first jaw spine having a proximal end; a second jaw spine having a proximal end, the second jaw spine being pivotally connected to the first jaw spine at a common pivot pin operably connected to the elongate tube to open and close the jaw spines in response to movement of the actuation rod; a first link having a distal end pivotally connected to the proximal end of the second jaw spine and a proximal end pivotally connected to a pivot pin on the actuation rod; and a second link having a distal end pivotally connected to the proximal end of the first jaw spine and a proximal end pivotally connected to the pivot pin of the actuation rod.

In another aspect, the surgical instrument of the invention comprises an elongate tube extending along an axis including an actuation rod; a first jaw spine having a proximal end and a distal end, the proximal end having a first series of gear teeth formed around a first hole; a second jaw spine having a proximal end and a distal end, the proximal end having a second series of gear teeth formed around a second hole, the second jaw spine being pivotally joined to the first jaw spine by a pivot pin through the first and second holes that operably opens and closes the jaw spines in response to movement of the actuation rod; and the elongate tube having a first fenestration of windows extending axially on one side of the tube and a second fenestration of windows extending on an opposite side of the tube facing the first fenestration of windows such that the first series of gear teeth can be positioned to ride within the first fenestration of windows and the second series of gear teeth can be positioned to ride within the second fenestration of window. With this aspect, when the actuation rod is drawn proximally within the elongate tube, the first and second series of gear teeth are pivoted on the pivot pin by the respective first and second fenestration of windows; and when the actuation rod is moved distally relative to the elongate tube, the first and second fenestrations of windows rotate the respective first and second series of gear teeth in opposite directions to an open position.

In yet another aspect, the invention is directed to a surgical instrument comprising an elongate tube extending along an axis including an actuation rod; a first jaw spine having a first cam slot, the first jaw spine being coupled to the elongate tube by a first pivot pin; and a second jaw spine having a second cam slot, the second jaw spine being coupled to the elongate tube by a second pivot pin, the second jaw spine being connected to the first jaw spine at a common pin attached to the actuation rod that rides within the first and second cam slots associated with the respective first and second jaw spines. When the actuation rod is moved distally, the common pin rides within the first and second cam slots causing the respective first and second jaw spines to rotate on the respective first and second pivot pins to an open position. When the actuation rod is pulled proximally relative to the elongate tube, the common pin moves to the proximal ends of the first and second cam slots causing the jaw spines to pivot on their respective first and second pivot pins to a generally closed position.

In another aspect, the invention is directed to a surgical instrument comprising an elongate tube extending along an axis including an outer tube and an actuation rod; a first jaw spine having a first cam slot, the first jaw spine being coupled to the outer tube by a first pivot pin disposed in the first cam slot; and a second jaw spine having a second cam slot, the second jaw spine being coupled to the outer tube by a second pivot pin disposed in the second cam slot, the second jaw spine being pivotally connected to the first jaw spine at a common pin attached to the actuation rod. When the actuation rod is moved distally relative to the outer tube, the first and second jaw spines pivot on the common pin as the respective first and second pivot pins ride within the respective first and second cam slots causing the first and second jaw spines to open.

In yet another aspect, the invention is directed to a surgical instrument comprising an elongate tube extending along an axis including an outer tube and an actuation rod; a first jaw spine having a first outer surface and a first stub extending outwardly of the first outer surface; and a second jaw spine having a second outer surface and a second stub extending outwardly of the second surface, the second jaw spine being pivotally connected to the first jaw spine by a common pin attached to the outer tube, wherein the actuation rod is bifurcated at its distal end to form two extensions that extend outwardly of the first and second surfaces, respectively. Each of the two extensions further comprises a slot, and the slots traverse one another and to the axis. Each of the slots of the two extensions is sized and configured to receive their respective first and second stubs associated with the respective first and second jaw spines. When the actuation rod is moved distally relative to the outer tube, the first and second stubs are forced to the distal end of their respective first and second slots causing the respective first and second jaw spines to close. When the actuation rod is pulled proximally relative to the outer tube, the first and second stubs are moved inwardly as they transition to the distal end of the respective first and second slots causing the respective first and second jaw spines to move to an open position.

These and other features and advantages of the invention will become more apparent with the description of the invention and reference to the associated drawings.

DESCRIPTION OF THE DRAWINGS

The accompanying drawings, which are included in and constitute a part of this specification, illustrate the embodiments of the invention and, together with the description, explain the features, advantages and principles of the invention. In the drawings:

FIG. 1 is a top plan view of a grasper of the invention including a single pivot pin and a double cam mechanism;

FIG. 2 is a bottom plan view of the grasper jaw of FIG. 1 illustrating in greater detail four camming surfaces associated with the jaws;

FIG. 9 is a top plan view of an actuation mechanism of a grasper jaw in accordance with another embodiment of the invention having a double pivot and slotted jaws;

FIG. 10 is a bottom plan view of the grasper jaw of FIG. 9;

FIG. 11 is a top plan view of an actuation mechanism of a grasper jaw in accordance with another embodiment of the invention including a double pivot and a double cam;

FIG. 12 is a bottom plan view of the grasper jaw of FIG. 11;

FIG. 13 is a top plan view of an actuation mechanism of a grasper jaw in accordance with another embodiment of the invention having a reversed slot with a pivot;

FIG. 14 is a bottom plan view of the grasper jaw of FIG. 13;

DESCRIPTION OF THE INVENTION

Figure 3:
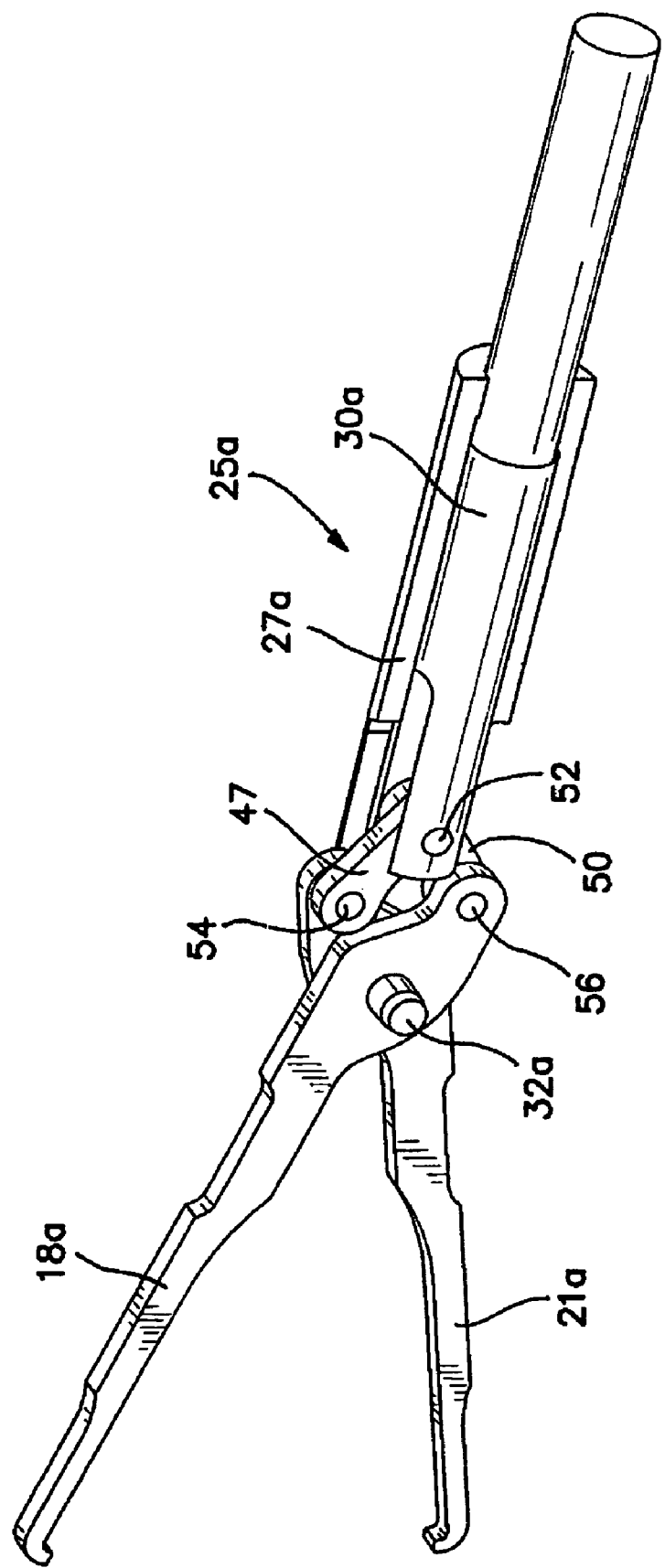
FIG. 3 is a perspective view of a grasper jaw in accordance with another embodiment of the invention including linkage in an actuation mechanism.

A surgical grasper is illustrated in FIG. 1 and designated by the reference numeral 10. The grasper is an elongate device having an axis 12 which extends between a proximal end 14 and a distal end 16. A pair of opposing jaw spines 18 and 21, disposed at the distal end 16, are operable between opened and closed positions by an actuation mechanism 23. A shaft assembly 25 extends along the axis 12 and includes an outer tube 27 and an inner actuation rod 30. The spines 18 and 21 are pivotally attached to the outer tube 27 by a common pivot pin 32.

The actuation mechanism 23 includes a distal camming pin 34 and a proximal camming projection 36. Both the pin 34 and projection 36 are carried by the actuation rod 30 which is moveable axially within the outer tube 27.

The camming pin 34 rides on two interior camming surfaces 38 and 41 each of which defines a slot in one of the jaw spines 21 and 18, respectively. When the actuation rod 30 is moved proximally, the camming pin 34 rides along the camming surfaces 38 and 41 and operates to close the jaw spines 18 and 21.

The camming projection 36 operates with respect to exterior camming surfaces 43 and 45 that are formed on the proximal side of the jaw spines 21 and 18, respectively. When the actuation rod 30 is moved distally, it rides on the exterior camming surfaces 43 and 45, and operates to open the jaw spines 18 and 21.

Thus, this embodiment includes two pairs of camming surfaces, namely the surfaces 38 and 41 and the surfaces 43 and 45, which can be disposed at different angles with respect to the axis 12. In this manner, the opening and closing of the jaws can be accomplished with different mechanical advantages. This enables the actuation mechanism 23 to be structured so that there is a higher mechanical advantage for closing the jaws when an increased load is encountered, and a lower mechanical advantage for opening the jaws when a higher speed may be desired.

In the embodiment of FIG. 3, elements of structure similar to those previously described are designated with the same reference numeral followed by the lower case letter "a." It can be seen that this embodiment includes the shaft assembly 25a, the outer tube 27a and the actuation rod 30a, as well as the jaw spines 18a and 21a that are pivotally connected on the common pivot pin 32a. However, in this embodiment the proximal ends of the jaw spines 18a and 21a are coupled to the actuation rod 30a by a pair of links 50 and 47, respectively. These links 47 and 50 are pivotally connected through a common pivot pin 52 to the actuation rod 30a. At their distal ends, the links 47 and 50 are individually connected to the jaw spines 21a and 18a, respectively. Thus, the link 47 is coupled to the jaw spine 21a by a pivot pin 54 and the link 50 is coupled to the jaw spine 18a through a pivot pin 56.

In operation, the embodiment of FIG. 3 also functions with the actuation rod 30a being moved axially relative to the outer tube 27a. When the actuation rod 30a is moved distally, the pivot pin 52 approaches the pivot pin 32a. This causes the distal ends of the links 47 and 50 to spread, resulting in the separation or opening of the jaw spines 18a and 21a. When the actuation rod 30a is pulled proximally relative to the outer tube 27a, the pin 52 moves away from the pin 32a causing the distal end of the links 47 and 50 to draw inwardly thereby closing the jaw spines 18a and 21a.

Figure 4:
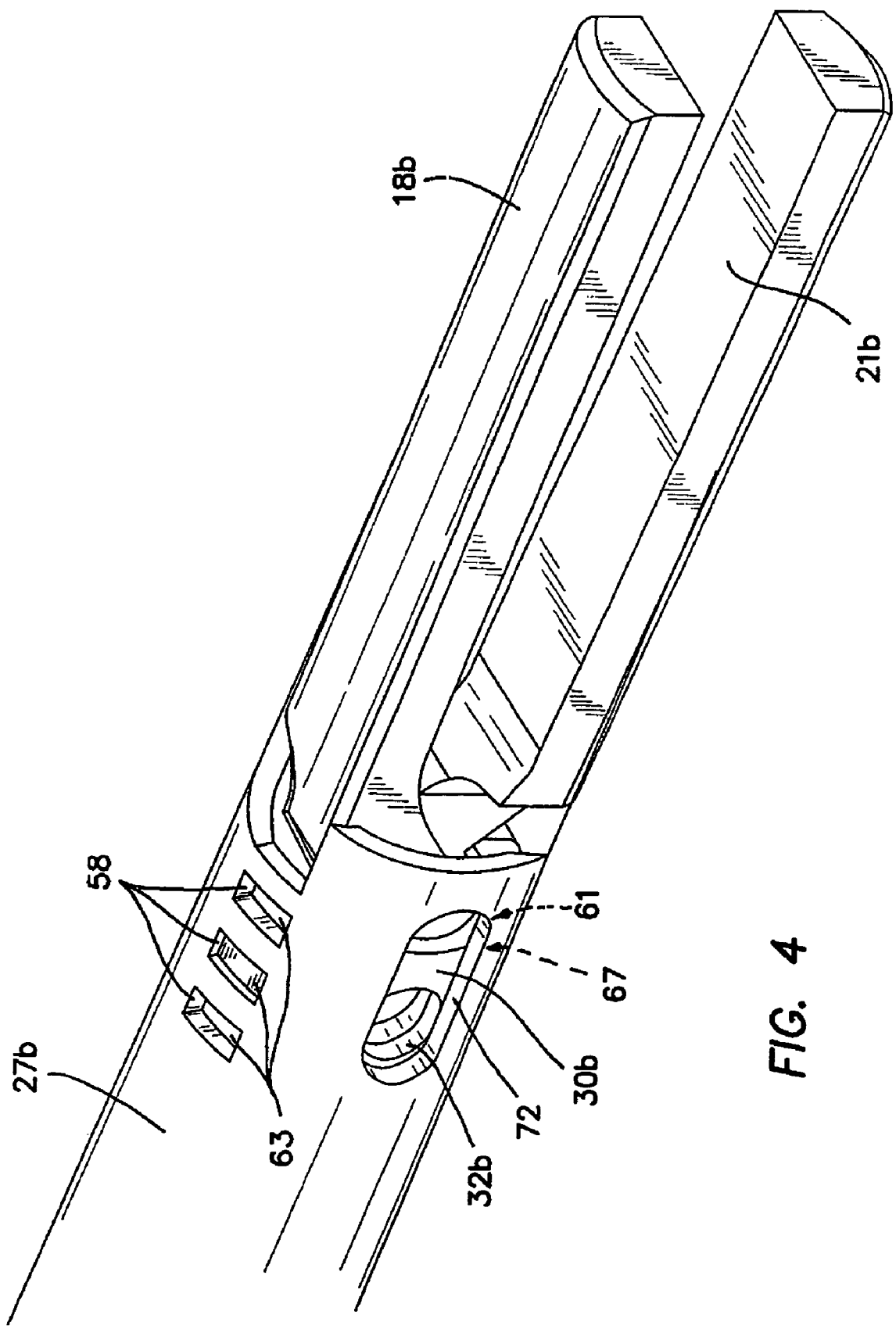
FIG. 4 is a perspective view of an actuation mechanism of a grasper jaw in accordance with another embodiment of the invention including a rack and pinion.

Referring to FIG. 4, elements of structure similar to those previously discussed will be designated with the same reference numeral followed by the lower case letter "b." Thus, this embodiment includes the outer tube 27b, actuation rod 30b, as well as the jaw spines 18b and 21b. In this case, the outer tube 27b is provided with a fenestration of windows 58 extending axially on one side of the outer tube 27b. A similar fenestration of windows 61 extends axially on the opposite side of the outer tube 27b.

Figure 6:
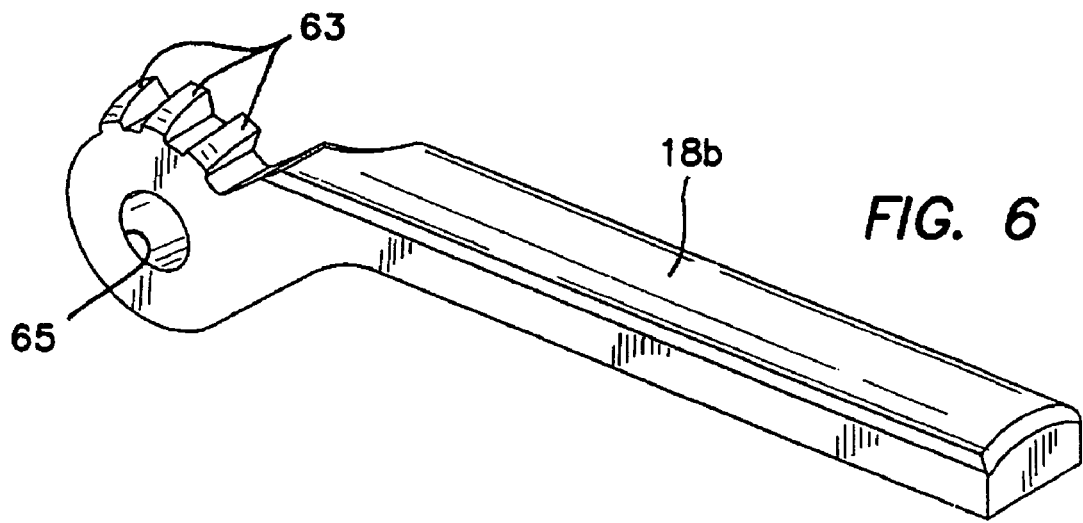
FIG. 6 is a top perspective view of the top jaw of the grasper jaw of FIG. 4.
Figure 7:
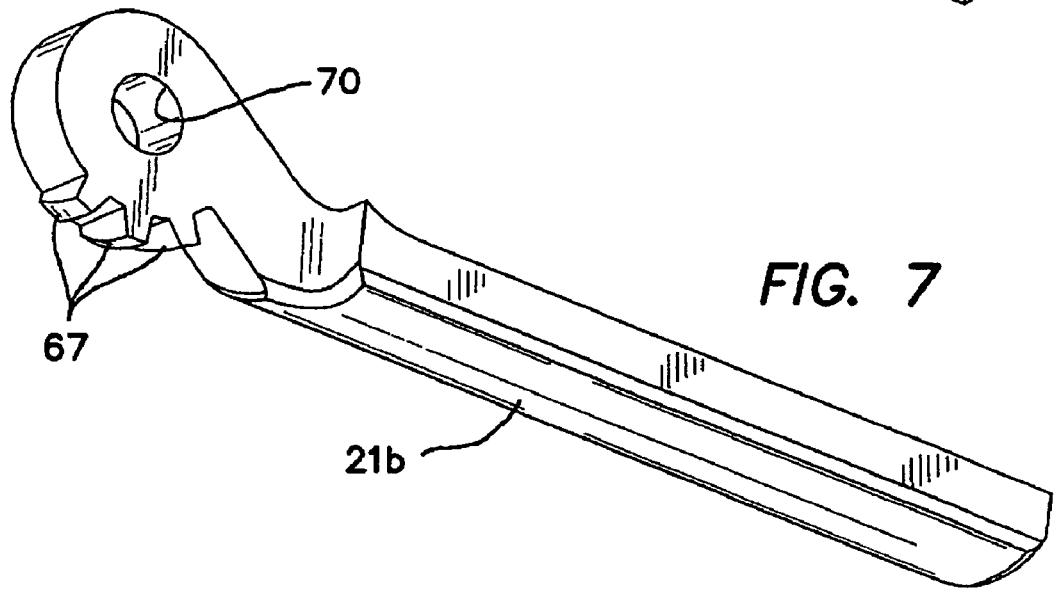
FIG. 7 is a bottom perspective view of the bottom jaw of the grasper jaw of FIG. 4.

The jaw spines 18b and 21b are best illustrated in the perspective views of FIGS. 6 and 7. On the proximal end of the jaw spine 18b, a series of gear teeth 63 are centered on a hole 65 that is offset from the longitudinal dimension of the jaw spine 18b. The jaw spine 21b is similarly constructed with a plurality of gear teeth 67 centered on a hole 70 that is offset from the longitudinal dimension of the jaw spine 21b.

In operation, the jaw spines 18b and 21b are joined by the pivot pin 32b (FIG. 5), which extends through the holes 65 and 70. The pin 32b can be further extended into at least one axial slot 72 in the outer tube 27b. This axial slot 72 is positioned between the fenestration of windows 58 and the fenestration of windows 61.

With this configuration, the gear teeth 63 of the jaw spine 18b can be positioned to ride within the fenestration of windows 58. Similarly, the gear teeth 67 of the jaw spine 21b can be positioned to ride within the fenestration of windows 61.

As with the previous embodiments, the actuation rod 30b is movable axially relative to the outer tube 27b. This movement is restricted in this embodiment by the length of the axial slot 72. When the actuation rod 30b is drawn proximally within the outer tube 27b, the gear teeth 58 and 67 are pivoted on the pin 32b by the fenestration of windows 58 and 61, respectively. With the windows 58 and 61 disposed on opposite sides of the outer tube 27b, the jaw spines 18b and 21b are moved in different directions, in this case to a closed position as illustrated in FIG. 4.

Figure 5:
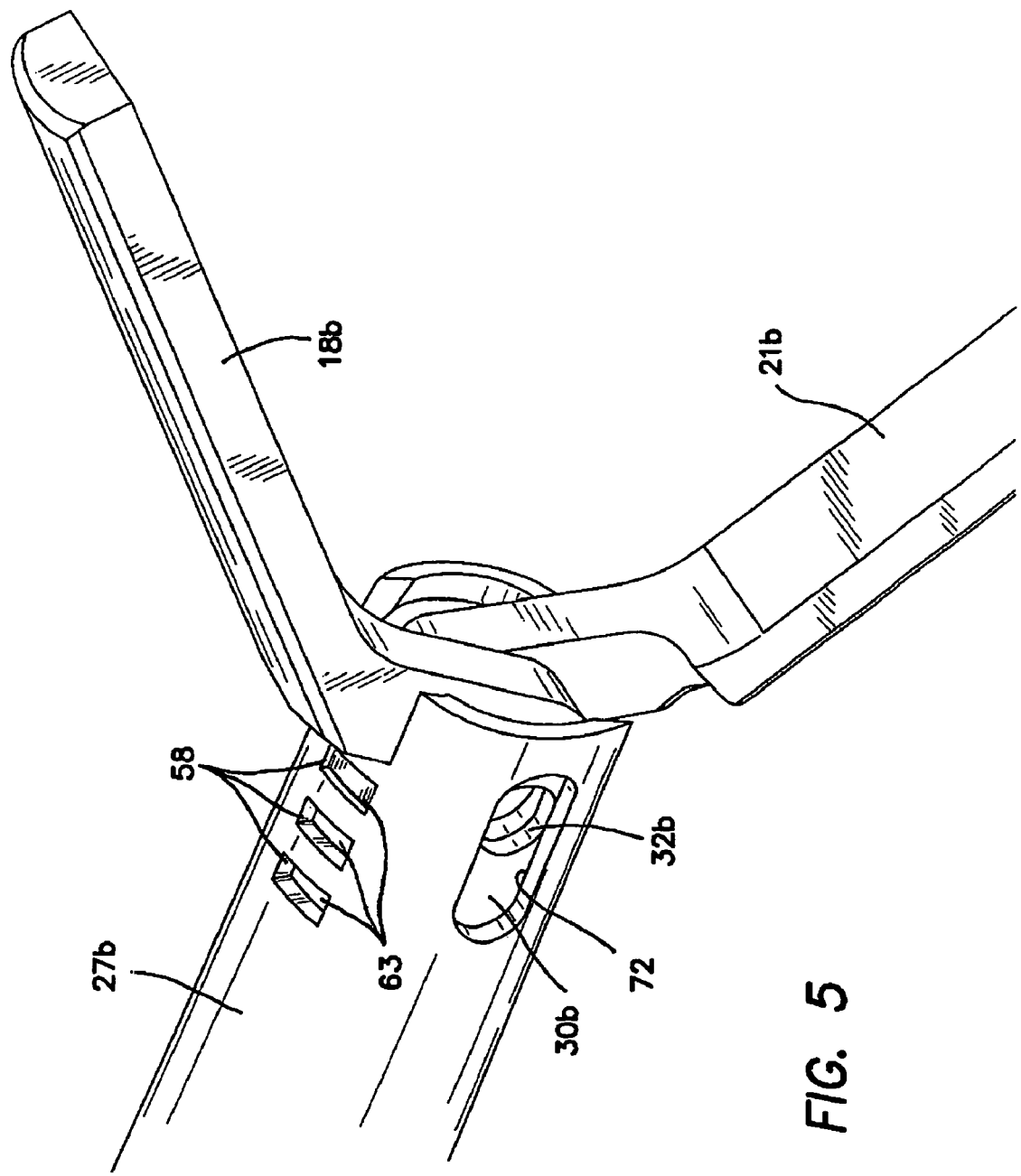
FIG. 5 is a perspective view of the actuation mechanism shown in FIG. 4 in an open position.

When the actuation rod 30b is moved distally relative to the outer tube 27b, the fenestration of windows 58 and 61 rotate the gear teeth 63 and 67, respectively, in opposite directions, in this case, to an open position as illustrated in FIG. 5.

Figure 8:
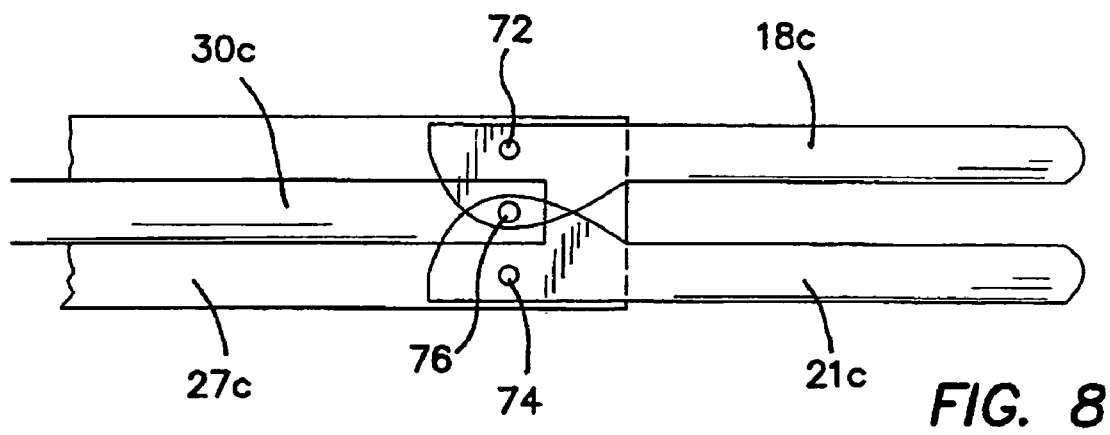
FIG. 8 is a side elevation view of an actuation mechanism of a grasper jaw in accordance with another embodiment of the invention including a separate pivot for each of the jaws.

Another embodiment of the invention is illustrated in the side elevation view of FIG. 8 where elements of structure similar to those previously discussed are designated with the same reference numeral followed by the lower case letter "c." Thus, in this embodiment the jaw spines are designated by the reference numeral 18c and 21c, while the outer tube and actuation rod are designated with the reference numerals 27c and 30c, respectively. As illustrated in FIG. 8, the jaw spine 18c is pivotally attached to the outer tube 27c by a pivot pin 72. Similarly, the jaw spine 21c is pivotally attached to the outer tube 27c by a pivot pin 74. The jaw spines 18c and 21c are also attached to the actuation rod 30c by a common pivot pin 76.

As in previous embodiments, the device is operated by moving the actuation rod axially relative to the outer tube 27c. With the common pivot pin 76 disposed inwardly of the individual pins 72 and 74, the actuation rod 30c can be pulled proximally relative to the outer tube 27c to close the jaw spines 18c and 27c. These jaw spines rotate on their individual pins 72 and 74 to a closed position as illustrated in FIG. 8. If the actuation rod 30c is pushed distally relative to the outer tube 27c, the jaw spines 18c and 27c rotate on their respective pivot pins 72 and 74 outwardly to an open position.

The embodiment of FIG. 9 contains elements of structure which are similar to those previously disclosed. In this case, these elements are designated with the same reference numeral followed by the lower case letter "d." Thus, this embodiment includes the outer tube 27d, the actuation rod 30d and the jaw spines 18d and 21d. The jaw spines 18d and 21d are coupled to the outer tube 27d by individual pivot pins 78 and 81, respectively. With this embodiment, a common pin 83 is provided that is attached to the actuation rod 30d, which rides within a pair of intersecting slots 85 and 87 associated with the jaw spines 21d and 18d, respectively.

As in previous embodiments, this device is operated by moving the actuation rod 30d axially relative to the outer tube 27d. When the actuation rod 30d is moved distally, the common pin 83 rides within the respective slots 85 and 87 of the jaws 21d and 18d. This causes the jaw spines 18d and 21d to rotate on the individual pivot pins 78 and 81, respectively, to an open position as illustrated in FIG. 9. When the actuation rod 30d is pulled proximally relative to the outer tube 27d, the common pin 83 moves to the proximal ends of the slots 85 and 87. This causes the jaw spines 21d and 18d to pivot on their respective pins 81 and 78 to a generally closed position.

In each of the above embodiments of the invention, the jaw spines such as jaw spines 18d and 21d can be overmolded with plastic to form a composite structure. In the example shown in FIG. 9, one of the composite jaws can be formed with the metal interior jaw spine 18d and an outer plastic overmold 90. A similar outer plastic overmold 92 can be formed on the metal jaw spine 21d. As noted, the plastic overmolds 90 and 92 can be easily and inexpensively provided with features such as a coupling detent 94 which is adapted to receive an atraumatic jaw pad 96. It is these features which can be easily and inexpensively molded into the plastic overmold 90 but which would be economically impossible to form on metal jaws. Thus the rigid composite jaw formed of the jaw spine 18d and overmold 90 is not only practical but also cost effective and accordingly facilitates the application of additional features such as the disposable atraumatic pads 96.

The embodiment of FIG. 11 is similar to that of FIG. 9 where elements of structure similar to those previously discussed are designated with the same reference numeral followed by the lower case letter "e." Thus, this embodiment includes the outer tube 27e, the actuation rod 30e, as well as the jaw spines 18e, 21e and associated overmolds 90e and 92e, respectively.

This embodiment is similar to that of FIG. 9 in that it includes the individual pins 78 and 81, as well as the common pin 83. In this embodiment, however, the common pin 83 is disposed to pivotally connect the jaw spines 18e and 21e with the actuation rod 30e. In other words, the common pin 83 is not disposed in slots, but rather is disposed in holes associated with the jaw spines 18e and 21e. By comparison, it will be noted that the individual pins 78 and 81 are not disposed in holes, as is the case with the embodiment of FIG. 9, but rather are disposed in associated slots.

In operation, as the actuation rod 30e is moved distally relative to the outer tube 27e, the jaw spines 18e and 21e pivot on the common pin 83e as the individual pins 78e and 81e ride within the respective slots 101 and 98. This movement causes the jaws 18e and 21e to open. Closure of the jaws 18e and 21e is achieved by drawing the actuation rod 30e proximally relative to the outer tube 27e.

A further embodiment of the invention is illustrated in FIG. 13 wherein elements of structure similar to those previously disclosed are designated with the same reference numerals followed by the lower case letter "f." Thus, this embodiment includes the outer tube 27f, actuation rod 30f, jaw spines 18f and 21f, overmolds 90f and 92f, as well as the common pivot pin 83f, and slots 98f and 101f. In this case, however, the slots 98f and 101f intersect so that the individual pins 81e and 78e (not shown) in the embodiment of FIG. 11 can be combined into a common pin 103 which is fixed to the outer tube 27f. With this exception involving the intersecting slots 98f and 101f in combination with the common pin 103, the embodiment of FIG. 13 functions in the same manner as that of FIG. 11.

Figure 15:
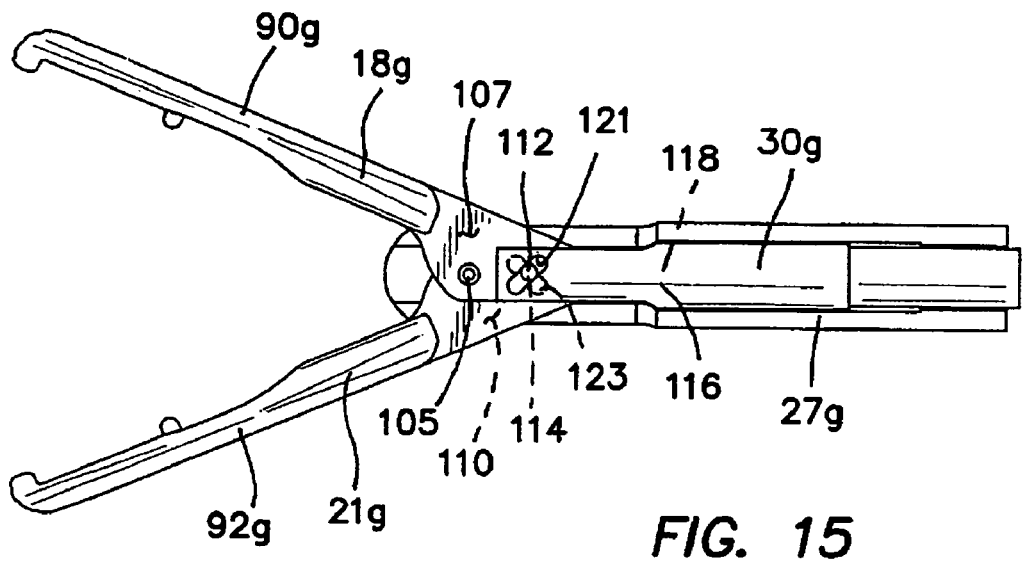
FIG. 15 is a top plan view of an actuation mechanism of a grasper jaw in accordance with another embodiment of the invention having a slotted actuation rod.
Figure 16:
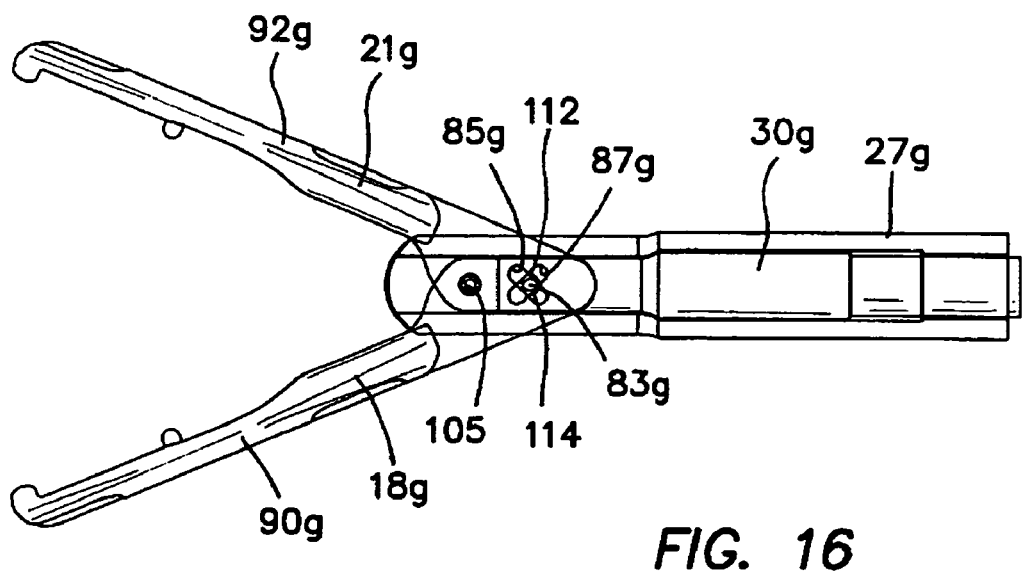
FIG. 16 is a bottom plan view of the grasper jaw of FIG. 15.

The embodiment of FIG. 15 contains elements of structure which are similar to those previously disclosed. Accordingly, they are designated with the same reference numerals followed by the lower case letter "g." Thus, this embodiment includes the outer tube 27g, the actuating rod 30g, the jaw spines 18g and 21g together with the associated overmolds 90g and 92g. In this embodiment, the jaw spine 18g has an outer surface 107 while the jaw spine 21g has an outer surface 110. A stub 112 is fixed, typically by welding, to the jaw spine 18g and extends outwardly of the surface 107. In a similar manner, a separate stub 114 can be fixed to the jaw spine 21g to extend outwardly from the surface 110. The jaw spines 18g and 21g are overlapped in a scissors configuration and held in a pivotal relationship with the outer tube 27g by a common pin 105.

The actuation rod 30g is bifurcated at its distal end to form two extensions 116 and 118 that extend outwardly of the surfaces 107 and 110, respectively. These extensions 116 and 118 are provided with slots 121 and 123, respectively, which are transversed to the axis 12g and also transverse to each other. In this embodiment, the slot 121 associated with the extension 116 is sized and configured to receive the stub 112 associated with the jaw spine 18g. Similarly, the slot 123 associated with the extension 118 is sized and configured to receive the stub 114 associated with the jaw spine 21g.

In operation, the jaw spines 18g and 21g pivot about the common pin 105 between an open position and a closed position. As the actuating rod 30g is moved distally relative to the outer tube 27g, the stubs 112 and 114 are forced to the distal end of their respective slots 121 and 123. This causes the jaw spines 18g and 21g to close as they move toward each other. When the actuating rod 30g is pulled proximally relative to the outer tube 27g, the stubs 112 and 114 are moved inwardly as they transition to the distal end of the respective slots 121 and 123. This causes the associated jaw spines 18g and 21g to move to an open position as they separate. When the actuating rod 30g is pushed distally relative to the outer tube 27g, the stubs 112 and 114 are moved outwardly as they transition to the proximal end of the respective slots 121 and 123. This causes the associated jaw spines 18g and 21g to move to a closed position as they come together.

There are many other embodiments of the invention which are operable with an actuating rod movable relative to an outer tube. Among these embodiments will be those which function by moving one of the jaw spines, such as the spine 18, with the actuating rod 30 and then moving the other of the jaw spines, such as the spine 21, with the first spine, such as the spine 18. Various configurations of common pins, individual pins, and slots can be used for these embodiments.

The invention claimed is:

1. A surgical instrument, comprising:
an elongate tube extending along an axis, the elongate tube having a lumen extending along the axis through at least a portion of the elongate tube;
an actuation rod positioned within the lumen and adapted to slide longitudinally along the axis of the elongate tube;
a first jaw spine having a proximal end and a distal end, the proximal end having a first series of gear teeth formed around a first hole;
a second jaw spine having a proximal end and a distal end, the proximal end having a second series of gear teeth formed around a second hole, the second jaw spine being pivotally joined to the first jaw spine by a pivot pin through the first and second holes that operably opens and closes the jaw spines in response to movement of the actuation rod; and
the elongate tube having a first fenestration of windows extending axially on one side of the tube and a second fenestration of windows extending on an opposite side of the tube opposing the first fenestration of windows such that the first series of gear teeth can be positioned to ride within the first fenestration of windows and the second series of gear teeth can be positioned to ride within the second fenestration of windows, the elongate tube further having an elongate slot formed therein, the elongate slot receiving a portion of the pivot pin.

2. The surgical instrument of claim 1, further comprising an atraumatic plastic overmold over each of the jaw spines.

3. The surgical instrument of claim 2, wherein the plastic overmold is molded with a coupling detent adapted to receive an atraumatic jaw pad.

4. The surgical instrument of claim 1, wherein the actuation rod is drawn proximally within the elongate tube.

5. The surgical instrument of claim 1, wherein when the actuation rod is drawn proximally within the elongate tube, the first and second series of gear teeth are pivoted on the pivot pin by the respective first and second fenestration of windows.

6. The surgical instrument of claim 1, wherein when the actuation rod is moved distally relative to the elongate tube, the first and second fenestrations of windows rotate the respective first and second series of gear teeth in opposite directions to an open position.

7. A surgical instrument, comprising:
an elongate tube;
an actuation rod longitudinally slidable within the elongate tube;
a first jaw spine having a first series of gear teeth; and
a second jaw spine having a second series of gear teeth, the second jaw spine being pivotally joined to the first jaw spine by a pivot pin that operably opens and closes the jaw spines in response to movement of the actuation rod; and
the elongate tube having means for engaging the first and second series of gear teeth;

wherein the means for engaging the first and second series of gear teeth comprises windows disposed in the elongate tube; and the elongate tube having an axial slot for engaging the pivot pin.

8. The surgical instrument of claim 7, further comprising an atraumatic plastic overmold over each of the jaw spines.

9. The surgical instrument of claim 7, wherein the actuation rod is movable proximally and distally within the elongate tube.

10. The surgical instrument of claim 9, wherein when the actuation rod is drawn proximally within the elongate tube, the first and second series of gear teeth are pivoted on the pivot pin by the means for engaging the first and second series of gear teeth.

11. The surgical instrument of claim 9, wherein when the actuation rod is moved distally relative to the elongate tube, the means for engaging the first and second series of gear teeth rotate the first and second series of gear teeth in opposite directions to an open position.

12. A surgical instrument, comprising:

an elongate tube having windows and an axial slot formed therein;

a first jaw spine having a first series of gear teeth arranged to engage the windows; and a second jaw spine, the second jaw spine being pivotally joined to the first jaw spine at a pivot joint, the first and second jaw spines rotatable in opposite directions to operably open and close and the pivot joint slidable in the axial slot relative to the elongate tube, such that a length of the axial slot defines limits of rotation of the first and second jaw spines.

13. The surgical instrument of claim 12, wherein the elongate tube has a second set of windows and the second jaw spine has a second series of gear teeth arranged to engage the second set of windows.

14. The surgical instrument of claim 12, further comprising an atraumatic plastic overmold over each of the jaw spines, one of the jaw spines being metallic.

* * * * *